US008661910B2

(12) United States Patent  
McLaughlin et al.

(10) Patent No.: US 8,661,910 B2
(45) Date of Patent: Mar. 4, 2014

(54) CAPACITIVE SENSOR

(75) Inventors: Patrick L. McLaughlin, Redmond, OR (US); Thomas D. Decker, Redmond, OR (US)

(73) Assignee: IPG, LLC, Redmond, OR (US)

( * ) Notice: Subject to any disclaimer, the term of this patent is extended or adjusted under 35 U.S.C. 154(b) by 1105 days.

(21) Appl. No.: 11/655,762

(22) Filed: Jan. 19, 2007

(65) Prior Publication Data

US 2008/0173303 A1 Jul. 24, 2008

(51) Int. Cl.
G01L 9/12 (2006.01)

(52) U.S. Cl.
USPC .............................. 73/718; 73/724

(58) Field of Classification Search
None
See application file for complete search history.

(56) References Cited

U.S. PATENT DOCUMENTS

| | | |
|---|---|---|
| 3,678,296 A | 7/1972 | Day |
| 4,057,205 A | 11/1977 | Vensel |
| 4,120,206 A * | 10/1978 | Rud, Jr. ............................ 73/718 |
| 4,393,714 A * | 7/1983 | Schmidt ........................... 73/718 |
| 4,651,728 A | 3/1987 | Gupta |
| 4,686,975 A | 8/1987 | Naimon |
| 5,052,400 A | 10/1991 | Dietz |
| 5,062,302 A * | 11/1991 | Petersen et al. ................ 73/754 |
| 5,134,886 A | 8/1992 | Ball |
| 5,195,528 A | 3/1993 | Hok |
| 5,492,129 A | 2/1996 | Greenberger |
| 5,558,086 A | 9/1996 | Smith |
| 5,603,315 A | 2/1997 | Sasso |
| 5,697,364 A | 12/1997 | Chua |
| 5,865,174 A | 2/1999 | Kloeppel |
| 6,213,955 B1 | 4/2001 | Karakasoglu |
| 6,220,244 B1 | 4/2001 | McLaughlin |
| 6,418,793 B1 | 7/2002 | Pechoux |
| 6,427,690 B1 | 8/2002 | McCombs |
| 6,470,885 B1 | 10/2002 | Blue |
| 6,532,958 B1 | 3/2003 | Buan |
| 6,575,163 B1 | 6/2003 | Berthon-Jones |
| 6,712,876 B2 | 3/2004 | Cao |
| 6,910,482 B2 | 6/2005 | Bliss |
| 6,925,884 B2 | 8/2005 | Hegner |
| 6,992,492 B2 | 1/2006 | Burdick |
| 7,013,898 B2 | 3/2006 | Rashad |
| 7,089,938 B2 | 8/2006 | Gale |
| 2002/0038657 A1 | 4/2002 | Yagi |
| 2003/0094047 A1 * | 5/2003 | Torkkeli ........................ 73/716 |
| 2004/0035422 A1 | 2/2004 | Truitt |
| 2006/0118115 A1 | 6/2006 | Cannon |
| 2006/0180149 A1 | 8/2006 | Matarasso |
| 2008/0000480 A1 | 1/2008 | Cannon |

(Continued)

OTHER PUBLICATIONS

US Office Action dated Jul. 5, 2012 issued in U.S. Appl. No. 12/472,853.

(Continued)

Primary Examiner — Andre Allen
(74) Attorney, Agent, or Firm — Workman Nydegger

(57) ABSTRACT

A capacitive sensor for measuring pressure comprises a fixed charge plate integral to a printed circuit board, a flexible charge plate that is grounded, a conductive donut-shaped adhesive spacer between the charge plates, a lid, a non-conductive donut-shaped adhesive spacer between the second charge plate and the lid, means of providing a pressure, fixed or variable, to both sides of the flexible charge plate, wherein a microcontroller controls a power supply and provides a voltage to the first charge plate wherein the accumulative voltage may be measured as a means of determining differential pressure.

26 Claims, 9 Drawing Sheets

(56) References Cited

U.S. PATENT DOCUMENTS

| | | |
|---|---|---|
| 2008/0035150 A1 | 2/2008 | Rittner |
| 2008/0053541 A1 | 3/2008 | Meckes |
| 2008/0078392 A1 | 4/2008 | Pelletier |
| 2008/0282880 A1 | 11/2008 | Bliss |
| 2009/0056708 A1 | 3/2009 | Stenzler |

OTHER PUBLICATIONS

Notice of Allowance dated Jan. 18, 2013 issued in U.S. Appl. No. 12/472,853.

* cited by examiner

SINGLE CAPACITOR

DUAL CAPACITOR

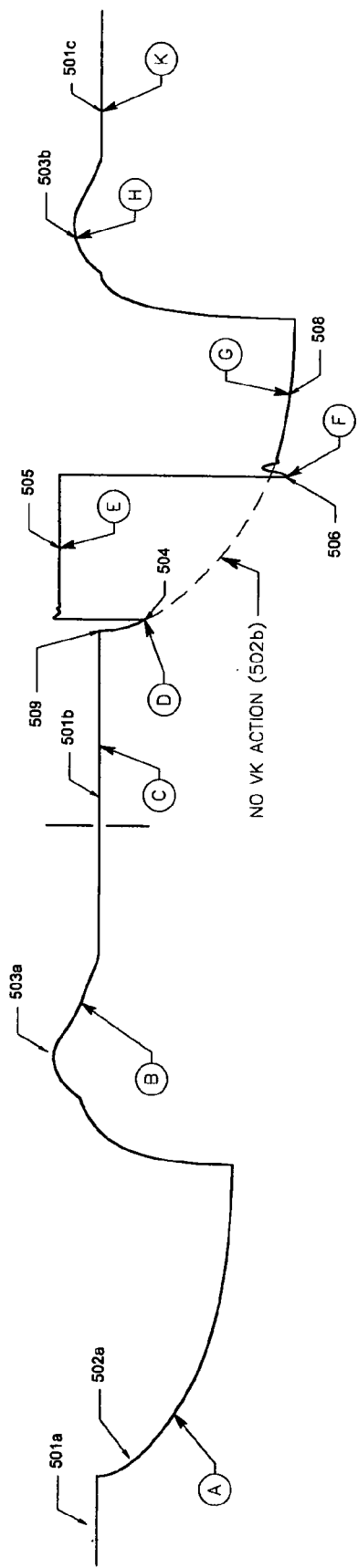

figure 5a

A: INSPIRATION NEGATIVE PRESSURE AS DETECTED FROM FEED-TUBE OF FACE MASK
B: POSITIVE EXPIREATION PRESSURES
C: NORMAL (ZERO PRESSURE) LEVEL
D: ALLOWABLE THRESHOLD INSPIRATION VALVE ON POINT
E: POSITIVE PRESSURE FROM (VK) VALVE ON (OXYGEN FLOWING APPROX 1 bar)
F: END OF OXYGEN FLOWING, FOLLOW THROUGH WITH INSPIRATION EFFORT
G: FOLLOWING OF INSPIRATION EFFORT
H: POSITIVE EXPIREATION PRESSURES
K: NORMAL (ZERO PRESSURE) LEVEL FIGURE 5b -- Breath Cycle showing Measurement Cycles

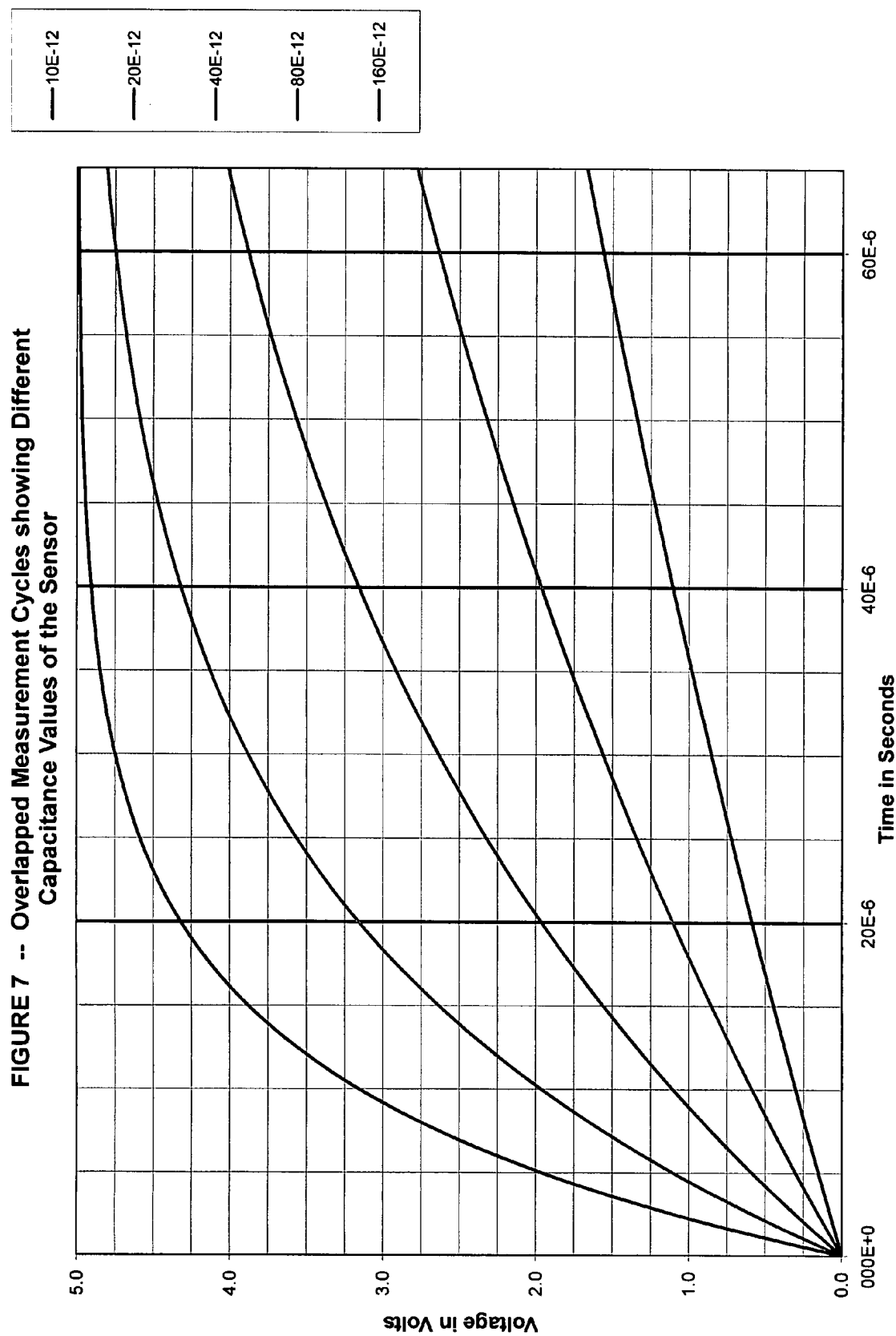
FIGURE 7 -- Overlapped Measurement Cycles showing Different Capacitance Values of the Sensor

CAPACITIVE SENSOR

II. CROSS REFERENCE TO RELATED APPLICATION

U.S. Pat. No. 6,220,244, "Conserving device for use in oxygen delivery and therapy", McLaughlin, is herein incorporated in its entirety by reference.

III. STATEMENT REGARDING FEDERALLY SPONSORED RESEARCH OR DEVELOPMENT

Not Applicable.

IV. REFERENCE TO SEQUENCE LISTING, A TABLE, OR A COMPUTER PROGRAM LISTING COMPACT DISC APPENDIX

Not Applicable.

V. BACKGROUND OF THE INVENTION

Refer to U.S. Pat. No. 6,220,244, "Conserving device for use in oxygen delivery and therapy", McLaughlin.

VI. BRIEF SUMMARY OF THE INVENTION

None included.

VII. DETAILED DESCRIPTION OF THE (INFORMAL) DRAWINGS

FIG. 7 depicts time-voltage curves for a single measurement cycle representative of various points in a respiratory cycle.

Note: headings provided herein are for convenience and do not necessarily affect the scope or interpretation of the invention.

VIII. DETAILED DESCRIPTION OF THE INVENTION

Figure 2A:
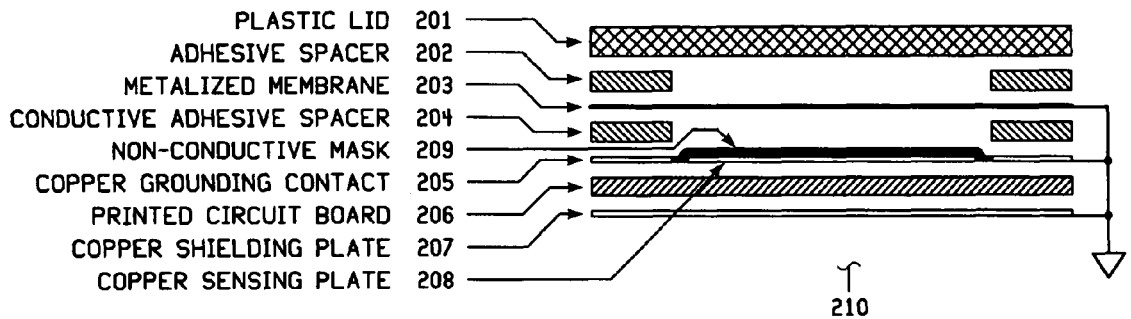
FIG. 2a is an exploded side view of a single capacitor sensor.

FIG. 2a depicts a preferred embodiment of the subject invention—a sensor assembly 210 including a single capacitor with at least one sensing plate. Sensor assembly 210 is preferably used as the sensing component of a pressure transducer. Pressure transducers have many applications which are well known in the art and related arts.

FIG. 2a specifically is an exploded, in part, side view of a single capacitive, or capacitor, sensor assembly 210—the invention may include the following fixedly stacked components: a plastic lid 201; a first adhesive spacer 202; a metalized membrane 203; a conductive adhesive spacer 204; a copper grounding contact 205; a PCB 206; a copper shielding plate 207; a copper sensing plate 208; and a non-conductive mask 209.

Figure 4:
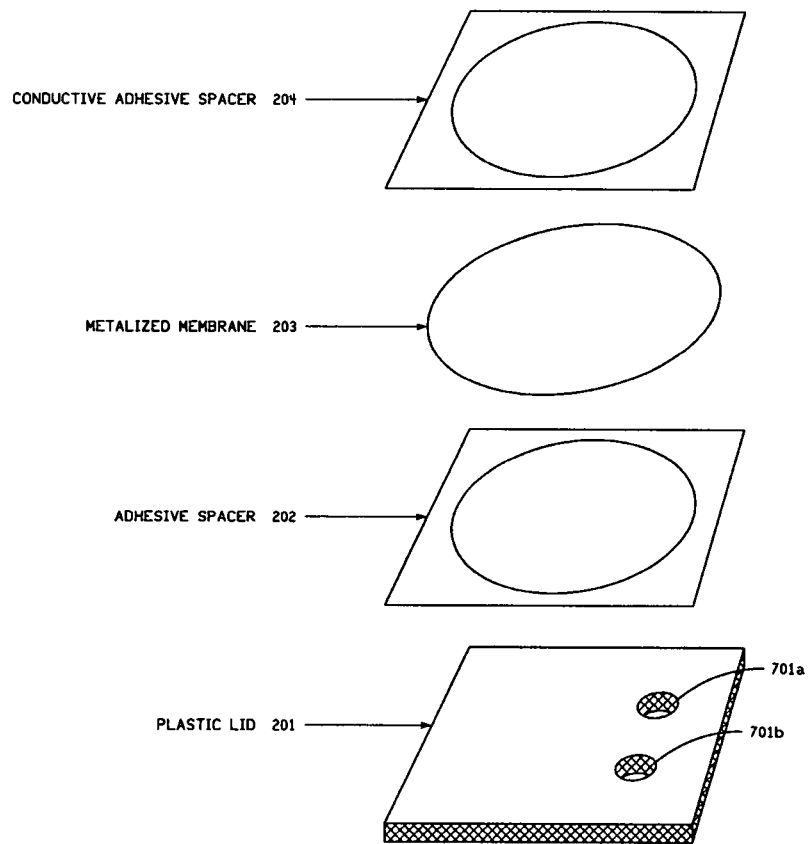
FIG. 4 is an exploded view of selected components of a single capacitor sensor.

FIG. 4 is an exploded perspective view of plastic lid 201; adhesive spacer 202, metalized membrane 203, and adhesive spacer 204 and includes the preferred location of ports 701a and 701b in plastic lid 201 when the subject invention is used with an oxygen delivery system for general aviation. Ports 701a and 701b are the ports of the corresponding apertures through lid 201 which enable the introduction of a first pressure, ambient or other, into chamber 219a and thereby to top side of the metalized membrane 203 when the stacked components are assembled. In this application of the invention the ports are preferably tubularly coupled with ambient pressure and are approximately 0.125 inches in diameter.

Figure 2B:
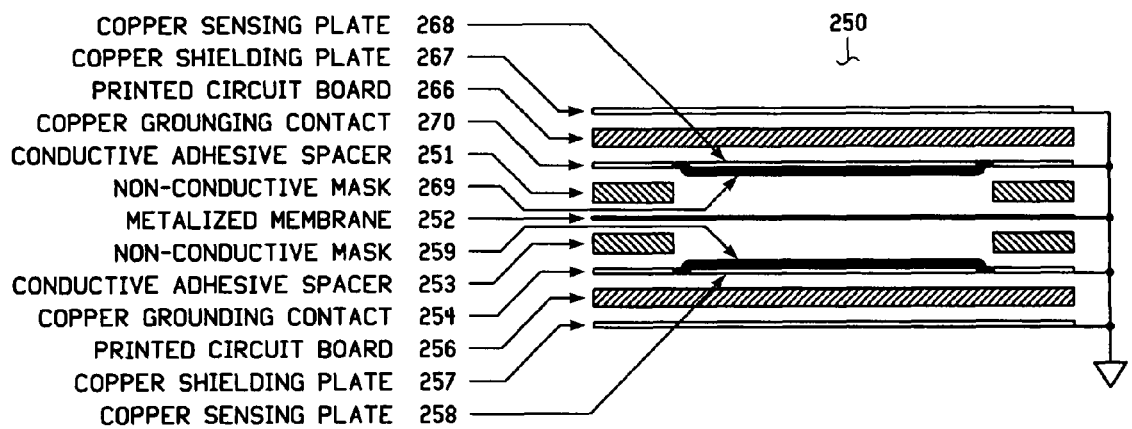
FIG. 2b is an exploded side view of a dual capacitor sensor.

FIGS. 2a and 2b do not depict apertures 701a or 701b nor do they depict means to introduce a second pressure to the bottom side of the metalized membrane 203—see chamber 219b. Aligned aperture through non-conductive mask 209, copper sensing plate 208, printed circuit board 206, and copper shielding plate 207 enable the introduction of a second pressure to the bottom side of the metalized membrane 203 via chamber 219b. In this application of the invention the port defined by these aligned apertures in copper shielding plate 207 (again, not shown) is pneumatically coupled with a cannula or face mask. Apertures are sized and placed so as to evenly and timely introduce pressure changes to chambers 219a and 219b and thereby metalized membranes 203 and 252 (see chambers 279a and 279b) and prevent damage to metalized membranes 203 and 252 in the event that the pressure, in either chamber (219a or 219b), is so great, or the opposite chamber (219b or 219a) negative pressure is so great, so as to deflect the membrane 203 or 252 into at least one aperture to damage it sufficiently to effect performance—e.g. plastic deformation.

The single capacitor sensor 210 in FIG. 2a is preferably used when accurate, precise, and timely pressure measurements are needed when the metalized membrane 203 deflects toward sensing plate 208. Dual capacitor sensor 250 as depicted in FIG. 2b would be a preferred alternative embodiment when accuracy, precision, and timeliness are needed when metalized membrane 203, or in FIG. 2b metalized membrane 252 deflects up or down—a true differential pressure sensor. One means of grounding the components in FIG. 2b is depicted.

Regarding the assembly of the single capacitor depicted in FIG. 2a, the first adhesive spacer 202 is a means for securely fixing the plastic lid 201 to metalized membrane 203 wherein the spacer 202 is preferably square with a round aperture and the first chamber 219a is defined therein. Preferably first adhesive spacer 202 is substantially non-conductive. Preferably the first chamber 219a is substantially sealed so the pressure therein may be controlled and accurately measured. The pressure may be a vacuum or preferably (and as described herein) the lid may have an aperture or port, or more than one, which may introduce a pressure—the pressure source may be regulated or controlled, or alternatively may be an unknown and uncontrolled. In the preferred application of the preferred embodiment of the invention two lid ports 701*a* and 701*b* are coupled to ambient pressure as part of a supplemental oxygen conserving delivery system for use in general aviation. The spacer 202 is preferably substantially non-conductive so as not to affect the charge on the membrane 203.

Alternatively the lid may be comprised of a second PCB 266. PCB 266 (or PCB 206) may originally include a copper laminate, or copper laminates, which may be etched to form copper sensing plates 268 and 258 (or copper sensing plate 208), and provide copper shielding plates 257 and 267 (or 207).

A second copper sensing plate 268 as illustrated in FIG. 2*b* will enable symmetrical sensing which may be a significant improvement for some true differential pressure sensor applications. And an additional copper shielding plate 267, which may be integral to the second PCB 266, will improve the performance of the dual capacitor sensor as preferably depicted in FIG. 2*b*.

Shielding plates 207, 257 and 267 provide electromagnetic shielding so metalized membranes 203 and 252 and copper sensing plates 208 and 258 and 268 respectively are electromagnetically isolated so as to improve the performance of the capacitive sensors.

Any of a number of alternative insulating, spacing, and securing means well known in the arts could be employed to achieve the function of spacer 202. Alternative means of defining a chamber 219*a* are may include a concave cavity (chamber) on the underside of lid 201 and alternative means for non-conductively securing the lid 201 to the membrane 203 including any of a number of adhesives well known in the art. Alternatively various manufacturing processes could be employed wherein these components and their functions could be combined into different, fewer or even a single part such as a plastic molded top that included the functions of lid 201 and means to affix to, and insulate from, membrane 203.

Preferably, the metalized membrane 203 is comprised of a flexible aluminized Mylar and is approximately 0.010 inches from the surface of the lid and 0.006 inches from non-conductive mask 209). This distance permits the lid 201 to act as a stop when the membrane experiences a significant pressure (negative pressure from the first pressure source in chamber 219*a* or positive pressure from a second pressure source in chamber 219*b*—see below). The stop prevents the membrane from experiencing excessive excursion which can be damaging, such as plastic deformation or premature fatigue from repeated excessive pressures/loads.

Conductive adhesive spacer 204 provides a means of grounding the membrane 203 and securing membrane 203 to the printed circuit board 206 and thereby defining chamber 219*b*.

As was the case with adhesive spacer 202 preferably adhesive spacer 204 is square with a round aperture therein, but any adequate aperture in the spacers could be equally functional and while it is preferred the spacers have the same dimensions it is not necessary. Alternative means of grounding the membrane 203 include a separate electrical contact between the membrane 203 and ground which is independent of the other components in FIG. 2*a* or wherein membrane 203 is grounded to copper grounding contact 205 independent of conductive adhesive spacer 204. Preferably membrane 203 is grounded via spacer 204 to copper grounding contact 205 (distinct from substantially insulated from copper sensing plate 208) on the PCB 206 when assembled (or etched there from).

The metalized membrane 203 is a first charge plate and the copper sensing plate 208 is a second charge plate of a capacitor. As described herein, printed circuit board 206 and sensing plate 208 preferably have apertures which share an axis such that they are coupled to a second pressure source which is introduced to chamber 219*b*. Preferably a non-conductive mask 209 may be disposed between the copper sensing plate 208 and the membrane 203 which will keep the metalized membrane 203 from shorting in the event it is deflected so as to come in contact with copper sensing plate 208.

An alternative embodiment, which does not conceptually depart from the single capacitor sensor depicted in FIG. 2*a* and described, preferably and alternatively herein, is depicted in FIG. 2*b*. Preferably this alternative embodiment includes all the components included in FIG. 2*b* but it can be appreciated that depending upon the application one skilled in the art could select from the additional components and their functions in FIG. 2*b* vis-avis FIG. 2*a* and enable a capacitive sensor. For example, the lid 201 in FIG. 2*a* may be replaced with another sensing plate—namely, copper sensing plate 268 and conductive adhesive spacer 251 but may not require PCB 266 or copper shielding plate 267 or non-conductive mask 269.

Alternatively, lid 201 may simply be replaced with printed circuit board 266 if the device needs another board—the PCB 266 could easily provide all the functions as lid 201. The non-conductive mask 269 and copper shielding 267 are preferred if this alternative is a dual capacitor sensor which requires a second sensing plate to enable the second capacitor—in this case copper sensing plate 268. The second sensing plate will provide for two capacitors which is preferred if the application is for a symmetrical differential pressure sensor. Obviously, and consistent with the embodiments described herein apertures in the conductive mask 269, copper sensing plate 268, copper shielding plate 267 and printed circuit board 266 would be necessary to maintain a port so as to introduce a pressure to chamber 279*a*. Introduction of a pressure to chamber 279*b* would be akin to the chambers 219*a* and 219*b* depicted in FIG. 2*a*.

Figure 1A:
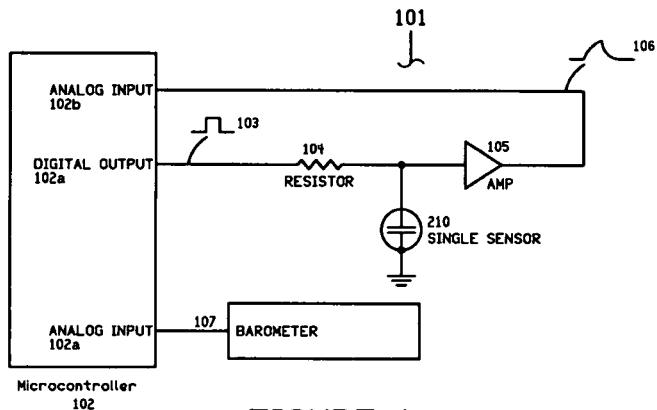
FIG. 1a is a schematic diagram illustrating a circuit for driving a single capacitor sensor.
Figure 1B:
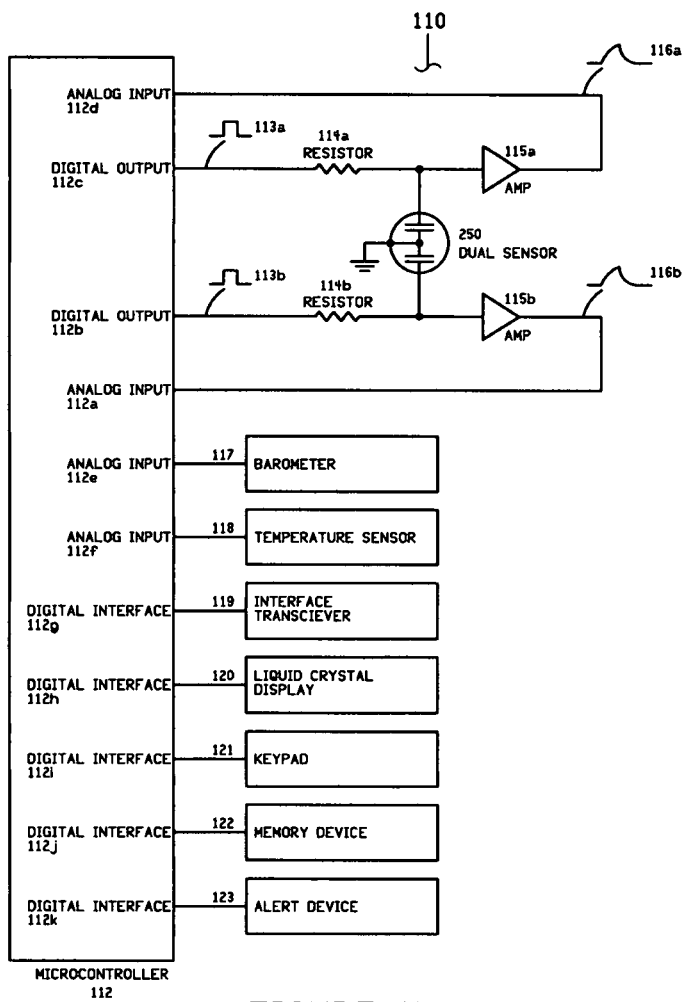
FIG. 1b is a schematic diagram illustrating a circuit for driving a dual capacitor sensor.

Capacitive sensors depicted in FIGS. 2*a* and 2*b* are driven by the circuits depicted in FIGS. 1*a* and 1*b* respectively. FIG. 1*a* depicts a simple RC circuit 101 which includes control means preferably a microcontroller 102—any of a number of adequate off the shelf controllers are well known in the art including Microchip PIC12C672 or PIC16F676. While the circuit can be driven any number of ways, for example the rise or fall times may vary or the voltage may vary, preferably a digital output 102*a* of microcontroller 102 is a pulse of 5 volts 103 (preferably the rise and fall times are 1 microsecond or less), which is applied through resistor 104 of a known value—preferably 1 M ohm. The resistor limits the current of the applied voltage and may vary based upon principles well-known in the electronic arts. An impedance buffer, preferably an operational amplifier 105, tracks the voltage and applies it to the analog-to-digital converter input 102*b* on the microcontroller 102 wherein the means for measuring the accumulated voltage takes place. The voltage source 103 and resistance 104 are of known values. The accumulated voltage across the capacitor for a given amount of time will therefore represent the distance between the charge plates in the single capacitive sensor 210. The components are calibrated and the microcontroller is programmed so the value of the capacitor varies with the air pressure placed upon it—thereby rendering a transducer. Preferably, the device is calibrated such that metalized membrane 203 is an initial distance from fixed charge plate (copper sensing plate) 208 when the pressures in chambers 219*a* and 219*b* are equal and deflects based upon the differential pressure in said chambers. So the pressure put upon the flexible charge plate (metalized membrane 203) can be calculated (by software or firmware or a functional equivalent preferably in or downloaded to the microcontroller 102)—from a single pressure source for absolute pressure or two pressure sources for differential pressure.

Figure 6:
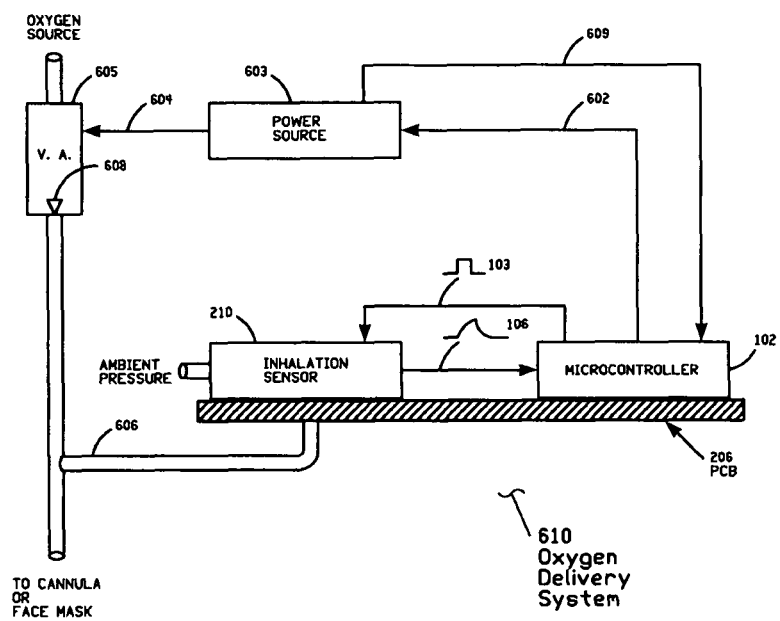
FIG. 6 is a schematic of an application of the invention in an electronic oxygen delivery system.

As depicted in FIG. 1a nd FIG. 2a, the preferred embodiment of the invention is not a true differential pressure sensor but a sensor for use in an oxygen delivery system wherein precise, accurate and timely data on exhalation is not necessary for desirable oxygen conservation. Deflection of membrane 203 toward sensing plate 208 preferably occurs during inspiration or inhalation and deflection toward lid 201 occurs during expiration or exhalation. Accurate, precise and timely data enables the timely delivery of a bolus of oxygen. As depicted in FIG. 6, the microcontroller output line 602 represents the conditioned signal from the sensor 210 for external use—in this case signaling valve assembly 605 to open valve 608 which enables a bolus of oxygen to be delivered to the user.

Figure 3A:
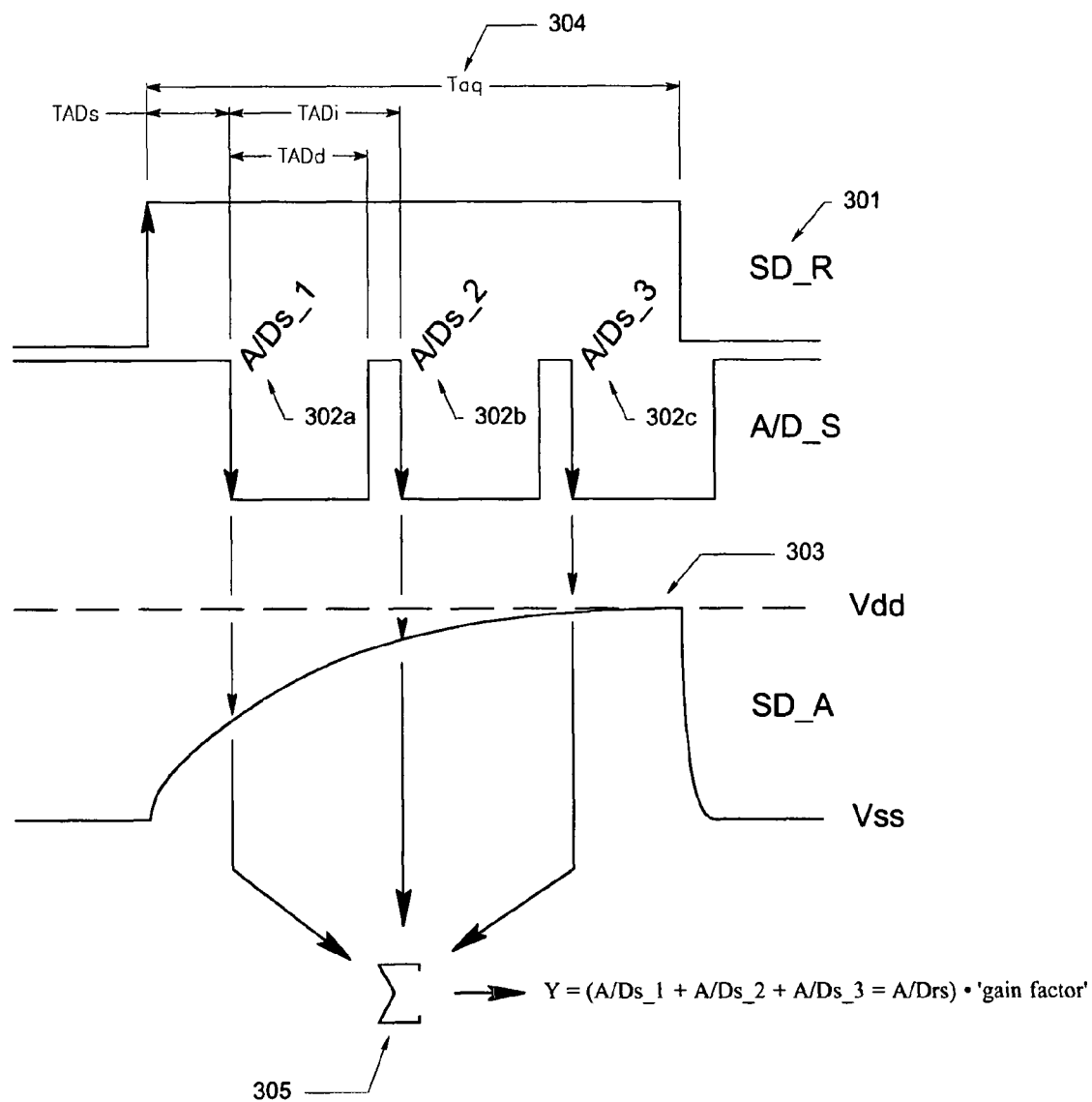
FIG. 3a is an event timing diagram with a corresponding asymptotic accumulation of voltage across a capacitive sensor and a summation thereof for a given pressure.

To illustrate a function of the RC circuit 101, refer to FIG. 3a. One measurement cycle starts with raising the voltage at SD_R 301 from zero to a known value—preferably 5 volts. This is followed by measuring the accumulated voltage across the capacitor at three points A/Ds_1, A/Ds_2 and A/Ds_3 (302a-c)—a single measurement cycle. Sigma 305 represents the addition of these three voltages and may be used to approximate the area under curve 303. Multiple measurements help zero out noise. This is followed with lowering the voltage to zero—see 306a and 306b for a time period that allows the capacitive sensor 210 to discharge to or near zero. Another measurement cycle cannot begin until sufficient time has elapsed for the capacitor to discharge to near zero. The zero point can be calibrated by the microcontroller 102 to a baseline if fast repetition rates are necessary. In the most preferred embodiment of the subject invention 16 measurement cycles are made and the values summed and conditioned (including averaging to reduce noise and improve the accuracy of the correlation between accumulated voltage and the pressure on metalized membrane 203) to create a value that closely approximates the area under the asymptotic curve 303. Other means of measuring the accumulated voltage may be employed—as long as these values are properly calibrated to represent a distance between the metalized membrane 203 and sensing plate 208 (which is preferably copper) and therefore a pressure. It should be noted that curve 303 may not be asymptotic—depending upon the circuit characteristics and the pulse characteristics the accumulated voltage may be linear or some other shape.

Figure 3B:
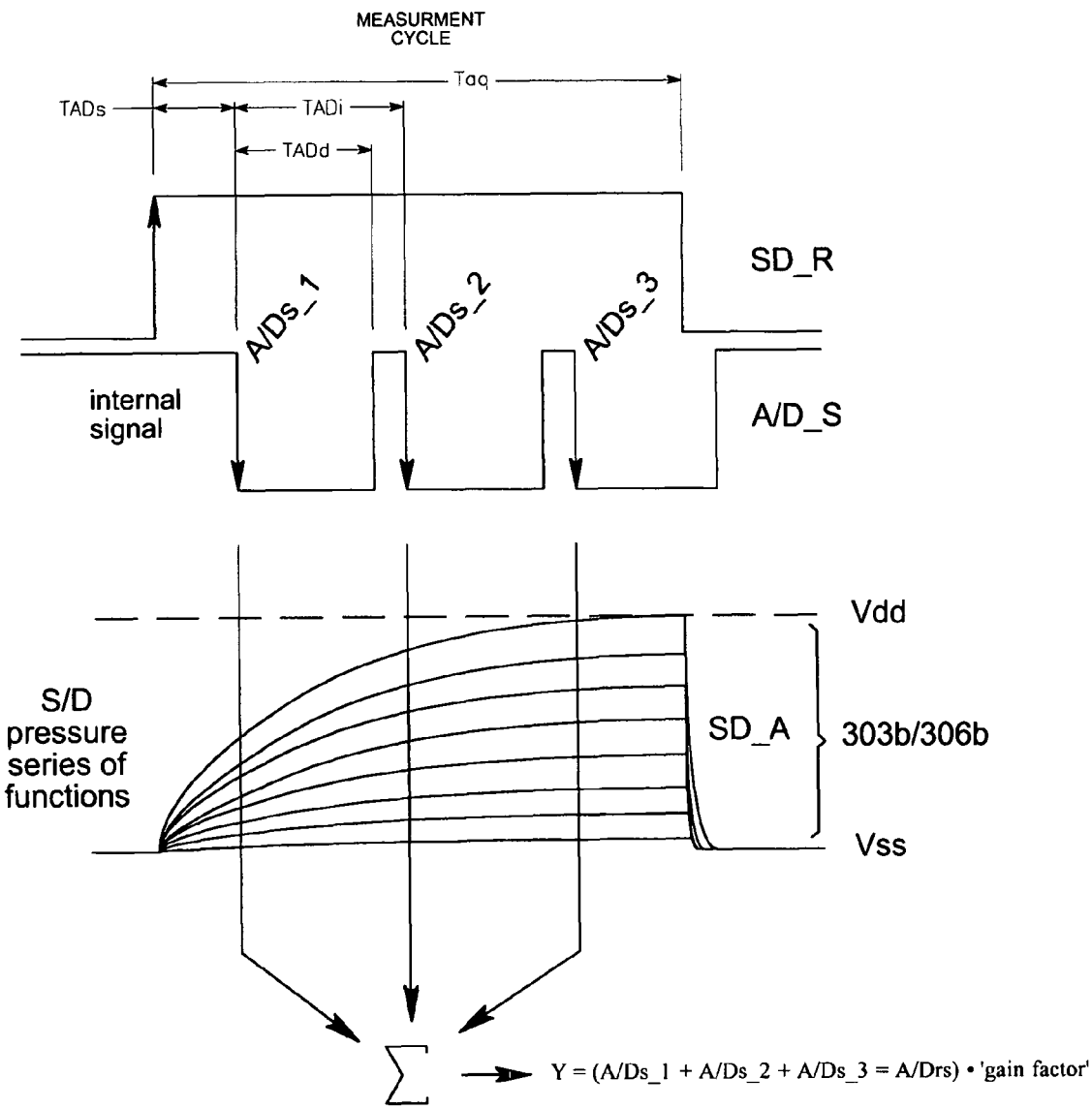
FIG. 3b is an event timing diagram with a corresponding asymptotic accumulation of voltage across a capacitive sensor and a summation thereof for variable pressures.

FIG. 3b illustrates a range of rates of accumulated voltage based upon the processes described in FIG. 3a—see SD_A2 in FIG. 3b. Each curve represents a different pressure put on membrane 203 which will be described in more detail. These values may be compared to other calculated values derived from the accumulated voltage to either determine a differential pressure in a true differential pressure sensor or alternatively if the capacitive sensor 210 is part of an electronic oxygen conserving delivery system (See FIGS. 5a, 5b and 6) as a means for tracking respiration to determine the optimal bolus of oxygen and the timing thereof.

FIG. 7 depicts time-voltage curves for a single measurement cycle representative of various points in a respiratory cycle—exhalation 801, no breathing 802, a small rate of inhalation 803, a moderate rate of inhalation 804 and large rate of inhalation 805. The x axis is time in seconds (note exponent)—accordingly 16 measurement cycles may be made in a fraction of a second.

Figure 5:
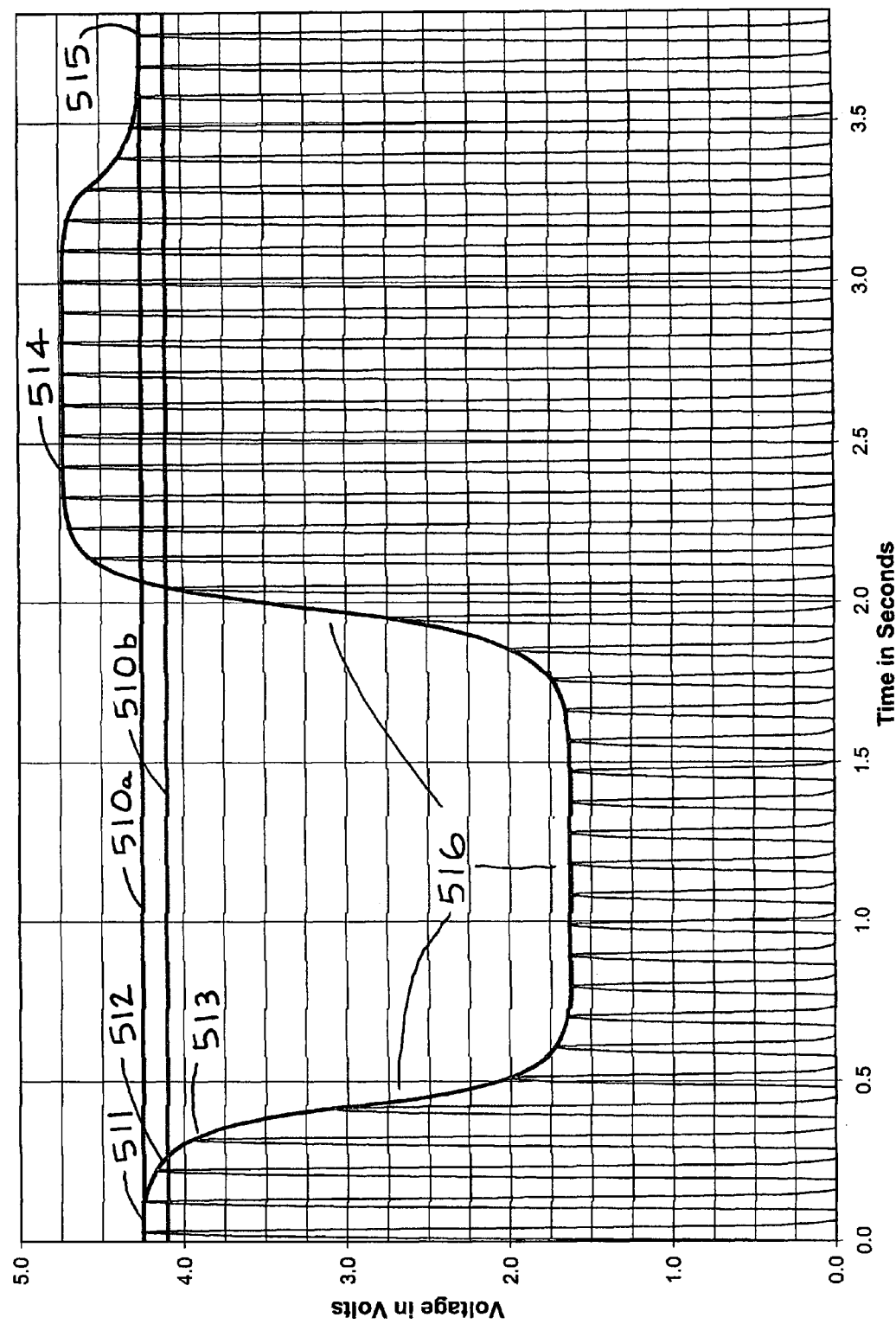
FIG. 5a is an event timing diagram of a waveform of 2 respiratory cycles with a bolus of oxygen delivered during the second inspiration event.
FIG. 5b is time-voltage curve of a single respiratory cycle derived from the amplitudes calculated from multiple measurement cycles.

FIG. 5a is an event timing diagram of a waveform of 2 respiratory cycles with a bolus of oxygen 505 delivered during the second inspiration event. Other embodiments of this application of the subject invention may deliver gases other than oxygen.

FIG. 5b is time-voltage curve of a single respiratory cycle derived from the amplitudes calculated from multiple measurement cycles. FIG. 5b illustrates how the data derived from the accumulated voltage in single capacitor sensor 210 and described in FIGS. 3a, 3b, and 7 is manipulated to construct the waveform representative of respiration or breathing. The accumulated measurements of voltage in FIG. 7 and FIGS. 3a and 3b, measured in seconds (note x axis exponent) are averaged and added to construct the wave form in FIG. 5b wherein 511 represents a state of no breathing, 512 represents the beginning of an inspiration event (510b trip threshold for breath detection), 513 represents when an inspiration event may be confirmed and a bolus of oxygen (preferably) is delivered, the area below the baseline (for no breathing) 510a and above respiration curve 516 estimates the total volume of inspiration, 514 represents expiration and 515 represents no breathing. Baseline 510a may represent zero pressure per calibration of the sensor 210, and may change based upon accumulated data from prior respiration events). It should be appreciated that other means of mathematical manipulation of the data derived from the accumulated voltage across sensor 210, or alternatively 250, may yield the same results if the system or device is properly calibrated.

To elaborate, in FIG. 5a 501a-c indicate zero pressure, that is, no inspiration or expiration which means membrane 203 is neither trending up or down for which it is calibrated. 502a-b indicate a negative pressure or inspiration. 503a-b indicate positive pressure or expiration. 504 indicates a triggering event wherein the microcontroller opens the valve 608 in the valve assembly 605 for a calculated time interval to provide a bolus 505 to the cannula or face mask. 502b (dotted line) indicates the inspiration superimposed by the bolus 505 and 508 indicates the follow-through of that inspiration event.

The bolus delivered to the inspiration tube 606 may be delivered to a delivery device such as a cannula or face mask. The bolus will vary depending upon the physical characteristics of the delivery device used by the patient or pilot. It should be appreciated that while the subject invention has been described for use in an oxygen delivery system there are many other applications, non-medical and medical for which it could be utilized. In particular the subject invention could be utilized in a respiratory monitoring system to detect, measure, and report respiratory characteristics based on calculated differential air pressures put upon sensor 210 or alternatively 250.

FIG. 1b depicts two simple RC circuits which drive the dual capacitor sensor 250. Microcontroller 112 serves the same functions as microcontroller 102 but drives an additional circuit, see digital outputs 112b and 112c and processes additional data, see analog inputs 112a and 112d. Other devices are depicted in FIG. 1b which may enhance the performance of the device such as barometer 117, which may be used to determine when a pilot may need supplemental oxygen among other uses. It is well known in the art of aviation that barometers are used to measure pressure altitude. Temperature sensor 118 may also provide data on ambient temperatures which may be useful in optimizing the performance of the device. The interface transceiver 119, LCD 120, keypad 121, and alert device 123 may facilitate the use and enhance the performance of the device. The memory device 112 may store respiration and system data to provide a record for later retrieval which may be used to monitor system performance.

Regarding microcontroller 112 (or 102) any of a number of adequate off the shelf controllers are well known in the art would suffice including Microchip PIC12C672 or PIC16F676. While the circuits depicted in FIGS. 1a and 1b may be driven any number of ways that are well known to those skilled in the art, the preferable means of driving the circuits in the dual capacitor sensor 250, see digital outputs 112c and 112b, is a 5 volt pulse 113a and 113b respectively, which is alternately applied through resistors 114a and 114b respectively, which are of a known value—preferably 1 M ohm. The resistor limits the current of the applied voltage and may vary based upon principles well-known in the electronic arts. Impedance buffers, preferably an operational amplifier 115a and 115b, tracks the voltage and applies it to the analog-to-digital converter inputs 112a and 112d on the microcontroller 112 wherein the means for measuring the accumulated voltages takes place. The voltage sources and resistances are of known values. The accumulated voltage across the capacitor for a given amount of time will therefore represent the position of metalized membrane 252 in dual capacitive sensor 250. The components are calibrated so the value of the capacitor varies with the net air pressure (see chambers 279a and 279b) placed upon metalized membrane 252, so the pressure put thereon can be calculated (by software or firmware or a functional equivalent preferably in or downloaded to the microcontroller 112)—the accuracy and precision of the dual capacitor sensor 250 is preferably symmetric.

FIG. 6 is a schematic of an oxygen delivery system 601 which conserves oxygen—an implementation of the subject invention. The inspiration sensor 210 resides on the PCB 206. The microcontroller 102 controls the power source 603 to provide a voltage 103 to a charge plate (either the flexible metalized membrane 203 or the fixed copper sensing plate 208 but preferably the sensing plate 208) in inspiration sensor 210. When an inspiration event is detected the microcontroller 102 sends an output signal 604 to the valve assembly 605 which opens valve 608 and a bolus 505 is delivered to inspiration tube 606. The power source 603 may simply be at least one off the shelf battery for a lightweight and/or portable oxygen delivery systems preferably operating at 4.2 volts. Alternatively, the power source may be external to the oxygen delivery system such as the typical 12 volt power available in general aviation aircraft. An adapter may be internal or external to the oxygen delivery system.

For an oxygen delivery system, or a respiratory monitoring system, preferably the first pressure source introduced to chamber 219a is ambient air and the second pressure source introduced to chamber 219b by the user via a respiratory tube 606.

The metalized membrane 203 or 252 is preferably a metalized Mylar. Due its properties it may be heated to predictably or controllably shrink, which increases the tension in the membrane, which controls the calibration point and may provide a robust and reliable sensor that is easy to make and easy to calibrate and which provides precise measurements in the capacitor 210.

An earlier version of the oxygen delivery system 601 is described in detail in the referenced U.S. Pat. No. 6,220,244 issued to the applicant. Many of the embodiments therein can be implemented into the subject oxygen delivery system including: a plurality of status indicators both visual and audio; power conservation methods and devices; means of measuring altitude to improve sensor performance and oxygen delivery performance—including changing the bolus; compilation of sensor data to more accurately detect the optimal time to deliver the bolus and duration of the bolus; and means of rejecting spurious data.

In regards to the means of detecting barometric pressure to detect changes in altitude, the barometric sensing device 107 or 117 may provide an input signal to the microcontroller when a sufficient change is altitude warrants a modification in oxygen delivery to the pilot or patient or indicates that supplemental oxygen must be used per laws and/or regulations.

While the '244 patent had a start drive line and sustain drive line in recognition that the solenoid valve in the valve assembly needed less power to be held open than to initially open, the subject invention saves power by going into pulse width modulation to not only use the least power possible to sustain an open valve but to change the duty cycle depending upon the power available—for example the battery voltage. This provides improved energy conservations.

The disclosed invention has been set forth in the forms of its preferred and alternative embodiments, and described for use in specific applications, but numerous modifications, which do not require independent invention, may be made to the disclosed devices, systems and methods without departing from inventive concepts embodied in the single capacitor sensor 210 which is disclosed and/or claimed herein.

Specifically, while an application of the subject invention discloses use in an oxygen conserving delivery system and certain embodiments have been directed to a system for pilots it should be assumed aspects of the subject invention and the embodiments thereof are equally applicable to general medicine wherein patients are in need of supplemental oxygen or medical treatment requires careful, accurate and timely respiratory monitoring. Moreover, the improved capacitive sensor may have myriad applications outside of general aviation or medicine.

What is claimed is:

1. A capacitive sensor element for differential pressure sensors, comprising:
a first fixed charge plate with a port coupled to a first pressure source;
a flexible charge plate;
means for securely separating the first fixed charge plate and the flexible charge plate wherein the charge plates are an initial distance apart;
means for electrically grounding the flexible charge plate;
a lid with a port coupled to a second pressure source;
means for securely separating the flexible charge plate and the lid;
means for providing a voltage to the first fixed charge plate;
means for measuring an accumulated voltage across the first fixed charge plate and the flexible charge plate for a given amount of time wherein the accumulated voltage is a function of a variable distance between the first charge plate and the flexible charge plate; and
means for calculating the differential pressure based on the change in the initial distance and the variable distance.

2. A capacitive sensor element according to claim 1, further comprising a printed circuit board wherein the first fixed charge plate is integral thereto and an aperture in the printed circuit board is aligned with the first fixed charge plate port.

3. A capacitive sensor element according to claim 2, further comprising a microcontroller which resides on the printed circuit board and wherein the microcontroller includes the means for measuring the accumulated voltage.

4. A capacitive sensor element according to claim 3, further comprising a power source wherein the microcontroller controls the power source to provide a voltage to the first fixed charge plate.

5. A capacitive sensor element according to claim 4, further comprising a resistor through which the microcontroller applies a pulse of voltage.

6. A capacitive sensor element according to claim 2, wherein print circuit board further comprises a means for electro-magnetic shielding the first fixed charge plate.

7. A capacitive sensor element according to claim 1, wherein the means for grounding is for the first fixed charge plate and wherein the means for providing a voltage is to the flexible charge plate and wherein the lid further comprises a means for shielding the flexible charge plate.

8. A capacitive sensor element according to claim 1, wherein the flexible charge plate is metalized Mylar.

9. A capacitive sensor element according to claim 1, wherein the means for securely separating the first fixed charge plate and the flexible charge plate is comprised of a first adhesive spacer.

10. A capacitive sensor element according to claim 9, wherein the first adhesive spacer is in electrical contact with the printed circuit board which further comprises the means for grounding the flexible charge plate.

11. A capacitive sensor element according to claim 1, further comprising means for non-conductively masking the first fixed charge plate from the flexible charge plate.

12. A capacitive sensor element according to claim 11, wherein the means for measuring the accumulated voltage resides in the microcontroller.

13. A capacitive sensor element according to claim 12, wherein the microcontroller is measuring an accumulation of voltage more than once for each of the pulses of voltage applied.

14. A capacitive sensor element according to claim 13, wherein the microcontroller measures more than one accumulation of voltage before a pressure is calculated.

15. A capacitive sensor element according to claim 12, further comprising a means of tracking the accumulated voltage in the microcontroller.

16. A capacitive sensor element according to claim 1, wherein the lid is a second fixed charge plate and the means for providing a voltage to the first fixed charge plate further comprises means to provide the voltage to the second charge plates.

17. A capacitive sensor element for absolute pressure sensors, comprising:
 a fixed charge plate with a port coupled to a pressure source;
 a flexible charge plate;
 means for securely separating the fixed charge plate and the flexible charge plate wherein the charge plates are an initial distance apart;
 means for electrically grounding the flexible charge plate;
 a lid;
 means for securely separating the flexible charge plate and the lid;
 means for providing a voltage to the fixed charge plate;
 means for measuring an accumulated voltage across the fixed charge plate and the flexible charge plate for a given amount of time wherein the accumulated voltage is a function of a variable distance between the first charge plate and the flexible charge plate; and
 means for calculating the pressure source.

18. A capacitive sensor element according to claim 17, wherein the fixed charge plate does not have a port and wherein the lid further comprises a port coupled to a pressure source.

19. A capacitive sensor element according to claim 17, wherein the means for grounding is for the first fixed charge plate and wherein the means for providing a voltage is to the flexible charge plate.

20. A capacitive sensor element according to claim 17, wherein the lid further comprises a means for shielding the flexible charge plate.

21. A capacitive sensor element according to claim 17, further comprising means for shielding the fixed charge plate.

22. A method of producing a capacitive pressure sensor assembly, comprising the steps of:
 (1) producing a fixed charge plate and a flexible charge plate;
 (2) securing and separating the fixed charge plate and the flexible charge plate a first distance apart;
 (3) providing means to ground the flexible charge plate;
 (4) producing a lid;
 (5) securing and separating the flexible charge plate and the lid;
 (6) providing means to apply a first pressure to one side of the flexible charge plate and means to apply a second pressure to the other side of the flexible charge plate;
 (6) providing means to apply a voltage to the fixed plate;
 (7) providing means to measure an accumulated voltage across the fixed charge plate and the flexible charge plate for a given amount of time wherein the accumulated voltage is a function of a variable distance between the fixed charge plate and the flexible charge plate; and
 (8) providing means to calculate a differential between the first pressure and the second pressure.

23. The method as defined in claim 22 wherein the method further comprises more than one measuring of the accumulated voltage.

24. The method as defined in claim 22 wherein the method further comprises applying a pulse of voltage to the capacitive sensor assembly.

25. The method as defined in claim 22 wherein the method further comprises a capacitive sensor assembly with a metalized Mylar charge plate.

26. The method as defined in claim 25 further comprising the steps of heating the metalized Mylar charge plate.

* * * * *